(12) United States Patent
Ferchmin et al.

(10) Patent No.: US 8,835,512 B2
(45) Date of Patent: Sep. 16, 2014

(54) THERAPEUTIC APPLICATION OF CEMBRANOIDS AGAINST HIV VIRUS REPLICATION, HIV-ASSOCIATED NEUROCOGNITIVE DISORDERS AND HIV VIRUS-INDUCED INFLAMMATION

(71) Applicants: Peter Andrew Ferchmin, San Juan, PR (US); Vesna Ana Eterovic, San Juan, PR (US); Jose Wigberto Rodriguez, Caguas, PR (US); Eddy Oscar Rios-Olivares, Guaynabo, PR (US); Antonio Henrique Baccin Martins, Guaynapo, PR (US)

(72) Inventors: Peter Andrew Ferchmin, San Juan, PR (US); Vesna Ana Eterovic, San Juan, PR (US); Jose Wigberto Rodriguez, Caguas, PR (US); Eddy Oscar Rios-Olivares, Guaynabo, PR (US); Antonio Henrique Baccin Martins, Guaynapo, PR (US)

( * ) Notice: Subject to any disclaimer, the term of this patent is extended or adjusted under 35 U.S.C. 154(b) by 0 days.

(21) Appl. No.: 13/649,828

(22) Filed: Oct. 11, 2012

(65) Prior Publication Data
US 2014/0107225 A1    Apr. 17, 2014

(51) Int. Cl.
*A61K 31/045*    (2006.01)
*A61K 45/06*    (2006.01)
*A61K 31/047*    (2006.01)

(52) U.S. Cl.
CPC .............. *A61K 31/047* (2013.01); *A61K 45/06* (2013.01)

USPC .......................................................... 514/738

(58) Field of Classification Search
USPC .......................................................... 514/738
See application file for complete search history.

(56) References Cited

U.S. PATENT DOCUMENTS 8,530,525 B2 *    9/2013    Ford et al. ............... 514/729
2009/0291976 A1 *    11/2009    Ferchmin et al. ......... 514/292

OTHER PUBLICATIONS

Sayed et al., "Biocatalytic and semisynthetic optimization of the anti-invasive tobacco (1S,2E,4R,6R,7E,11E)-2,7,11-cembratriene-4,6-diol", 2008, Bioorganic & Medicinal Chemistry, 16(6), pp. 2886-2893.*
Rodriguez et al., "Modulation of HIV-1 Replication, Inflammation, and Neurotoxicity by a Tobacco Cembranoid 4R: Therapeutic Implications for HIV-Associated Neurocognitive Disorders", Oct. 2010, Journal of Neurovirology, vol. 16, No. Suppl. 1, p. 73, P157.*
Rodriguez et al., "Tobacco Cembranoid 4R Attenuates HIV Neurotoxicity by Glutamate Release Reduction Independent of Viral Replication and Inflammation", Apr. 2011, Journal of Neuroimmune Pharmacology, vol. 6, No. Suppl. 1, pp. S56-S57.*

* cited by examiner

*Primary Examiner* — My-Chau T Tran
(74) *Attorney, Agent, or Firm* — Lawrence Harbin; Harbin & Hein PLLC

(57) ABSTRACT

A method and composition for suppressing replication of the HIV-1 virus strains, modulating the production and liberation of inflammatory mediators; and the prevention and treatment of neurocognitive disorders. The method comprises administering to a subject an effective amount of an a macrocyclic diterpenoid, such as 4R cembranoid.

10 Claims, 13 Drawing Sheets

THERAPEUTIC APPLICATION OF CEMBRANOIDS AGAINST HIV VIRUS REPLICATION, HIV-ASSOCIATED NEUROCOGNITIVE DISORDERS AND HIV VIRUS-INDUCED INFLAMMATION

STATEMENT REGARDING FEDERALLY SPONSORED RESEARCH AND DEVELOPMENT

This invention was made with government support under NIH-NINDS U01NS063555, NIH-NCRR G12RR03035 (RCMI) and NIH-NCRR 1U54RR0261393 awarded by National Institutes of Health grants. The government has certain rights in the invention.

RELATED APPLICATIONS

This application further claims the benefits of priority U.S. Provisional Application 61/546,017 filed on Oct. 11, 2011.

BACKGROUND OF THE INVENTION

1. Field of the Invention

The present invention relates to the field of medical prevention and treatment of a neuroinjury; in particular, relates to the prevention and treatment of HIV (Human immunodeficiency virus) infection and HIV-associated neurocognitive disorders (HAND).

2. Discussion of the Background

Currently there are several antiviral drugs for the treatment of HIV/AIDS. However, one of the main problems with antiviral drugs is the mutation of the virus and the HIV virus is not an exception. Some treatments were developed to extend the life of the person infected with the virus. For example one of the treatments is called HAART (Highly Active Antiretroviral Therapy), which is a treatment to suppress HIV viral replication and the progression of HIV disease. HAART is defined as treatment that comprises at least three active anti-retroviral medications (ARV's), typically two nucleoside or nucleotide reverse transcriptase inhibitors (NRTI's) plus a non-nucleoside reverse transcriptase inhibitor (NNRTI) or a protease inhibitor (PI) or another NRTI called abacavir (Ziagen).

In addition there is a concern for HIV replication stimulated by inflammatory mediators, such as cytokines and chemokines. Therefore there is a major need to identify a compound that can prevent synthesis and liberation of proinflammatory cytokines and chemokines.

Further in the post-HAART era, HIV-associated neurocognitive disorders (HAND) have become the most common neurologic complication of AIDS, affecting approximately 40-60% of HIV-infected patients. HAND is an encephalopathy induced by HIV-1 infection and fueled by immune activation of T-lymphocytes and macrophages. These activated cells have the capability to enter the brain and secrete neurotoxins of both host and viral origin affecting brain cells such as glial cells and neurons. There is a major need to identify a compound that can prevent or alleviate the damaging effects following HIV-1 infection in the brain.

Several studies, as disclosed in US Patent Application 2009/0291976 and US Patent Application 2011/0015186, hereby included by reference, have identified a non-toxic compound called 4R-cembranoid (4R), a cyclic diterpenoid from the family of cembranoids, a natural product found in tobacco leaves and flowers that readily penetrates into the brain and has demonstrated anti-apoptotic, anti-inflammatory, and neuroprotective properties:

Neuroprotection: 4R protects the brain against N-methyl-D-aspartate (NMDA)-induced excitotoxicity. This was extensively studied in ex viva (brain slices) and briefly in vivo (Ferchmin et al., 2005). U.S. Pat. No. 6,204,289 B1, Issued: Mar. 20 2001

Anti-apoptotic: 4R stimulates certain NMDA receptors activating a prosurvival and anti-apoptotic process which involves increase of intracellular calcium, activation of the PI3-Kinase/Akt cascade followed by GSK-3beta inactivation (Ferchmin et al., 2005). U.S. patent application Ser. No. 12/308,293 (pending)

Anti-inflammatory: 4R inhibits COX with an $IC_{50}$ lower than acetylsalicylic acid (Olsson et al., 1993).

Therefore is a need to identify a effective dose of a compound that can diminish inflammatory mediators and prevent or alleviate the damaging effects following HIV-1 infection in the brain.

SUMMARY OF THE INVENTION

The present invention has identified a non-toxic terpenoid called 4R-cembranoid (4R) that readily penetrates into the brain and has anti-apoptotic, anti-inflammatory, and neuroprotective properties. The first object of the present invention is to provide a method using an effective dose of 4R-cembranoid to suppress HIV-1 replication in T-lymphocytes by administering to a subject an amount of 4R.

Another aspect of the invention is to modulate the production of inflammatory cytokines/chemokines in these HIV-infected cells.

Another aspect of the invention is to identify the amount of 4R which is toxic to glial cells and neurons.

Another object of the invention is to diminish HIV-mediated neurotoxicity.

The invention itself, both as to its configuration and its mode of operation will be best understood, and additional objects and advantages thereof will become apparent, by the following detailed description of a preferred embodiment taken in conjunction with the accompanying drawing.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings which are incorporated herein constitute part of the specifications and illustrate the preferred embodiment of the invention.

DESCRIPTION OF THE PREFERRED EMBODIMENT

The accompanying drawings which are incorporated herein constitute part of the specifications and illustrate the preferred embodiment of the invention.

Figure 1:
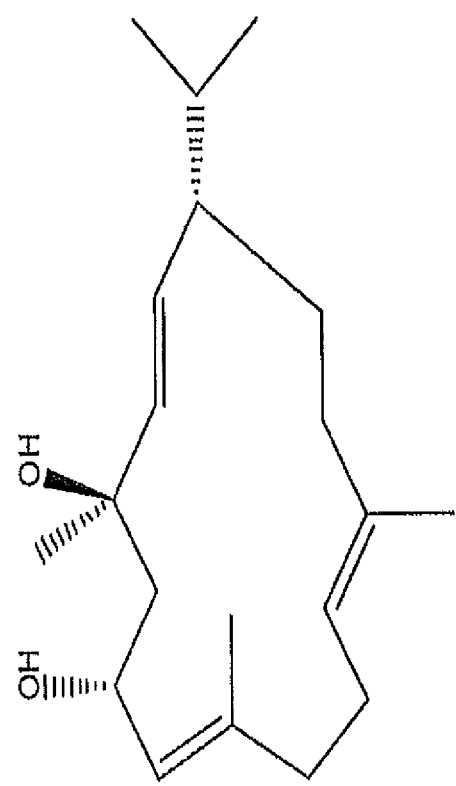
FIG. 1 shows the chemical structure of the 4R-Cembranoid in accordance with the principles of the present invention.

FIG. 1 shows the general Structure of the present invention chemical formula 4R-cembranoid.

Figure 2:
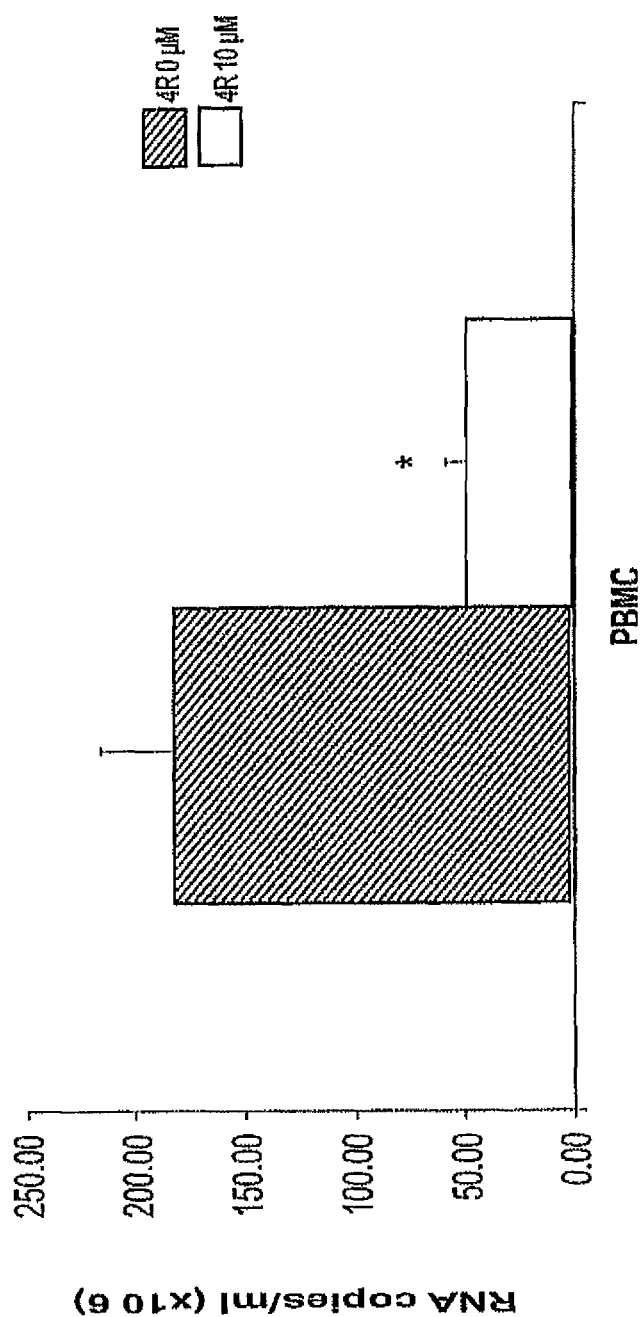
FIG. 2 shows graphical results of 4R decreasing HIV-1 virus replication in Peripheral Blood Mononuclear Cells (PBMC).

FIG. 2 is directed to the effect of 4R treatment on HIV viral load in acutely HIV-1 infected peripheral blood mononuclear cells (PBMC). PBMC from healthy donors were infected with HIV-1 SF2 for 6 days. Before infection cells were pretreated with 4R (10 µM) for 24 hours. After pretreatment, PBMC were infected with HIV-1 SF2 and 24 hours later, 4R (10 µM) was added. Subsequently, the cells were treated with 4R every 72 hours. Control cultures received 4R vehicle, dimethyl sulfoxide (DMSO) at the same times. Viral load was measured by RT-PCR method (Reverse transcription polymerase chain reaction).

The results show that with human PBMC acutely infected with HIV-1 virus, (10 µM) 4R decreased HIV-1 virus replication to 28% of the control value obtained in the absence of 4R.

Figure 3:
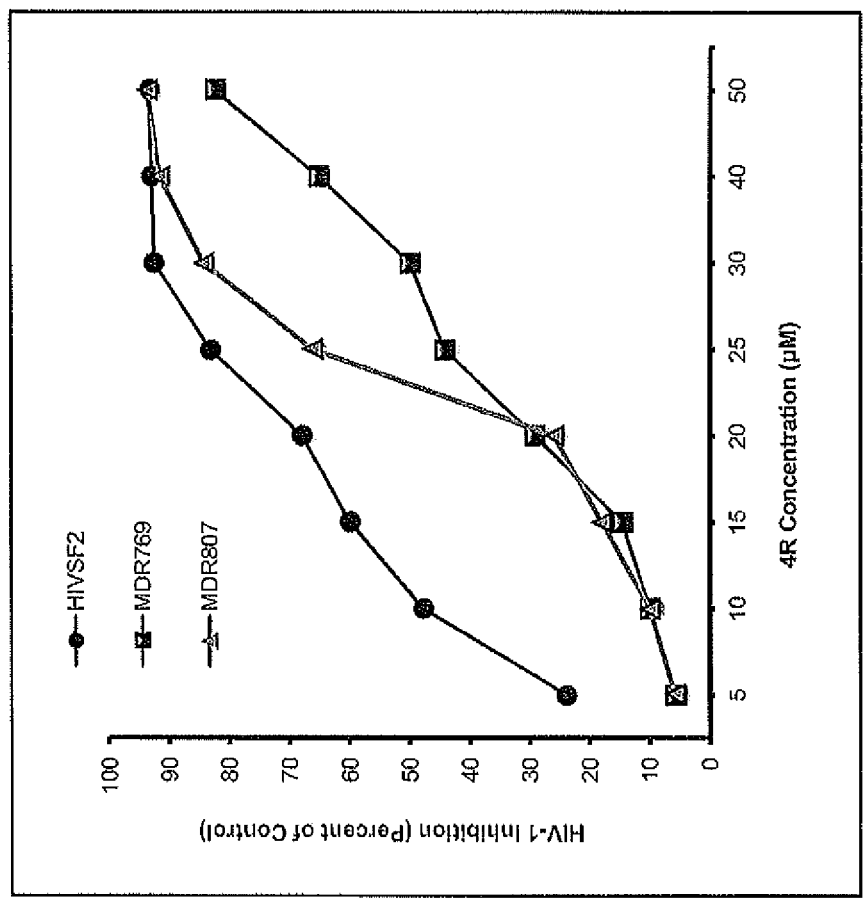
FIG. 3 shows graphical results of 4R decreasing the replication of two AZT-resistant HIV-1 virus strains in Peripheral Blood Mononuclear Cells (PBMC).

FIG. 3 is directed to the effect of 4R treatment on the replication of two AZT-resistant HIV-1 virus strains in Peripheral Blood Mononuclear Cells (PBMC). Approximately $2.0 \times 10^6$ PBMC were infected with the HIVSF2 strain and two AZT-resistant HIV-1 strains (MDR769 and MDR807) for 24 hours. After washing with medium, the cells were treated with various 4R concentrations. At 6 days post-infection, HIV p24 levels were measured. The data shown represent experiments performed in quadruplicate.

The results show that 4R inhibited close to 90% of the HIV p24 of the infected cells compared to infected cells alone.

Figure 4:
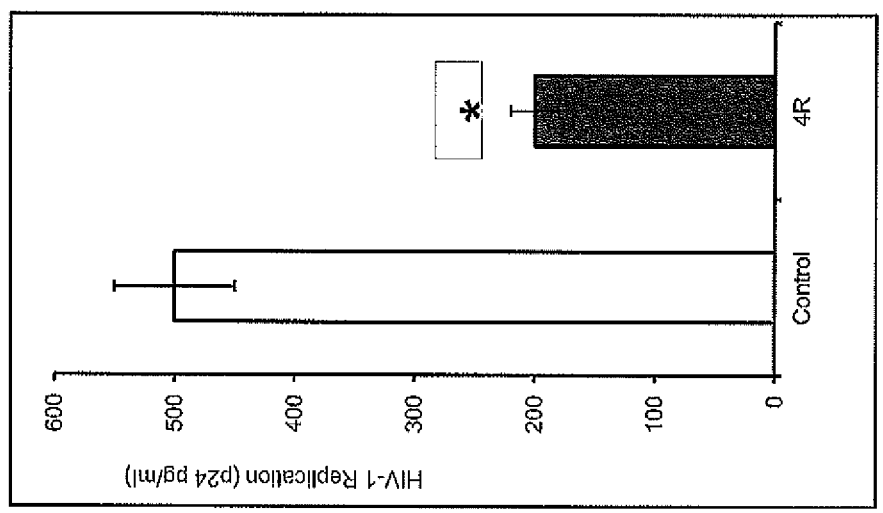
FIG. 4 shows graphical results of 4R decreasing HIV-1 virus replication in human microglial cells.

FIG. 4 is directed to the effect of 4R treatment on HIV viral load in acutely HIV-1 infected human microglial cells. Approximately $1.0 \times 10^6$ human microglia cells were infected with long of HIV-1 Bal for 24 hours. After washing with medium, the cells were treated with 40 µM of 4R compound. At 6 days post-infection, HIV p24 levels were measured. The data shown represent three independent experiments performed in quadruplicate.

The results show that 4R inhibited 60% of the HIV p24 of infected cells compared to the vehicle control.

Figure 5:
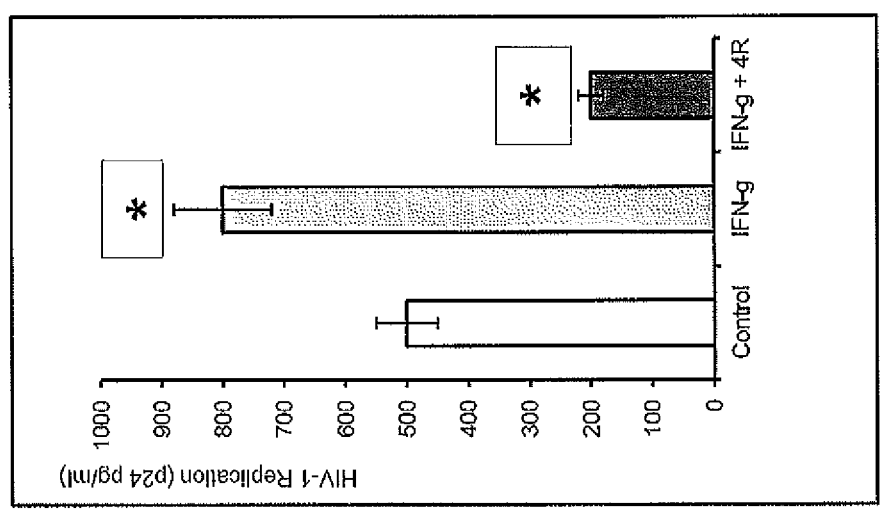
FIG. 5 shows graphical results of 4R decreasing HIV-1 virus replication in human microglial cells in the presence or in the absence of interferon-g (IFN-g).

FIG. 5 is directed to the effect of 4R treatment on HIV viral load in acutely HIV-1 infected human microglial cells, in the presence of interferon-g (IFN-g). Approximately $1.0 \times 10^6$ human microglia cells were infected with long of HIV-1 Bal for 24 hours. After washing with medium, the cells were treated with interferon-g (IFN-g) in the absence and in the presence of 40 µM of 4R compound. At days post-infection, HIV p24 levels were measured. The data shown represent three independent experiments performed in quadruplicate.

The results show that, in the presence of IFN-g, 4R inhibited 75% of the HIV p24 of infected cells compared to the IFN-g control.

Figure 6:
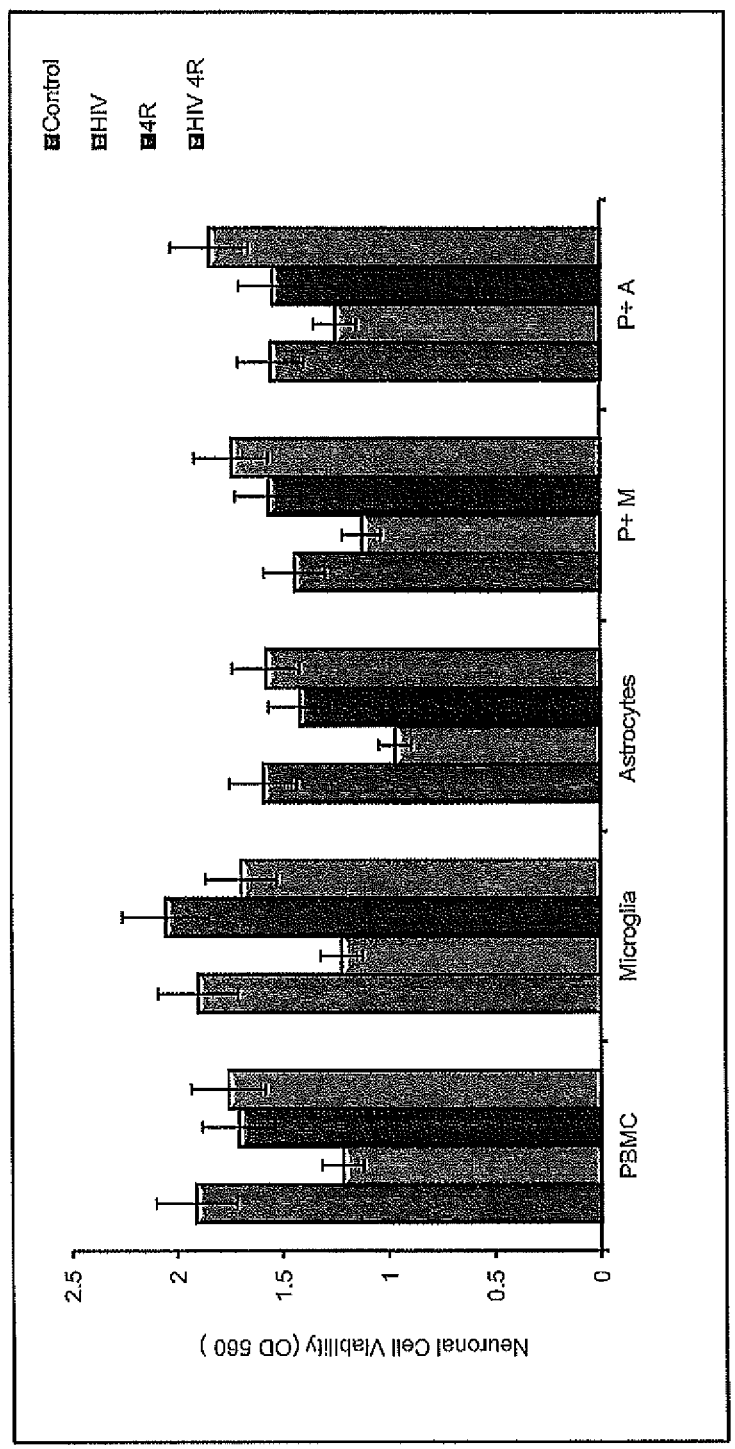
FIG. 6 shows graphical results of 4R preventing the HIV-1 virus-induced neurotoxicity.

FIG. 6 discloses the effect of supernatants from HIV-infected human glia cells and PBMC, in the presence or absence of 4R, added to a human neuronal cell line for 48 hours. Neurons viability was measured by MTT. Supernatants from cells infected with HIV-1 virus decreased neuronal survival by approximately 20%-40% (compare first and second bar in each set as shown in FIG. 6). On the other hand, supernatants from not infected cells not treated and treated with 10 µM 4R had no effect on neuronal viability (compare first and third bar in each set as shown in FIG. 6). Finally, supernatants from cells infected with HIV-1 virus and treated with 10 µM 4R did not display increased neuronal death (compare first and last bar in each set as shown in FIG. 6).

The results show that 4R prevented the HIV-1 virus induced neurotoxicity.

Figure 7:
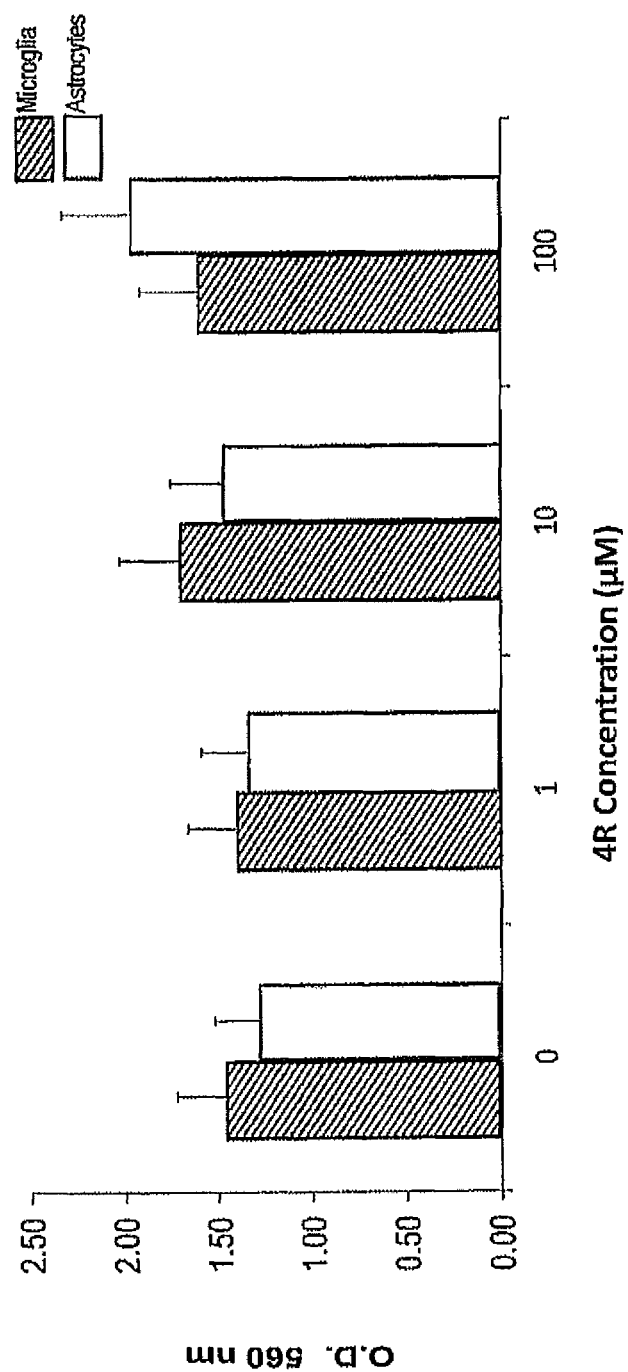
FIG. 7 shows graphical results for the lack of toxicity of 4R to microglia and astrocyte cells.

FIG. 7 is directed to human microglia and astrocyte cell lines treated for six days with 4R at various concentrations (1-100 µM). The number of cell remaining in the well at day 6 was measured by applying colored solutions to the cells in order to quantify cells by measuring them at a certain wavelength by a spectrophotometer. For example a MTT (3-(4,5-Dimethylthiazol-2-yl)-2, 5-diphenyltetrazolium bromide) reagent which produces a blue color proportional to the number of live cells. The color is measured as optical density (O.D.) at the wavelength of 560 nm.

The results show that 4R is not toxic to these cell lines up to a concentration of 100 µM.

Figure 8:
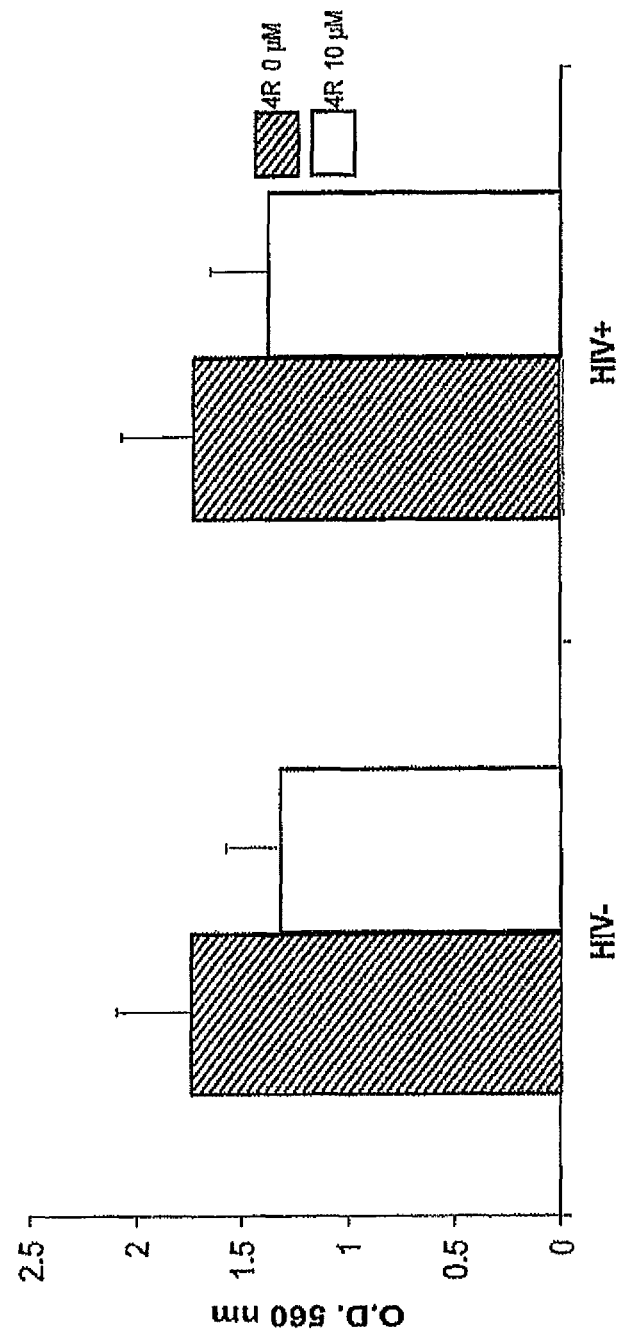
FIG. 8 shows graphical results of the lack of toxicity of 4R to neurons, in the presence or absence of HIV-1 virus.

FIG. 8 is directed to human neuronal cell line infected with HIV-1 SF2 and treated for six days with 10 µM 4R. The number of cells remaining in the well at day 6 was measured with the MTT reagent which produces a blue color proportional to the number of live cells. The color is measured as optical density (O.D.) at the wavelength of 560 nm.

The results show that 10 µM 4R is not toxic to neurons in the presence or in the absence of HIV-1 virus. Note that the virus itself was not toxic to neurons which do not have a receptor for this virus and subsequently neurons cannot be infected by HIV-1 virus. The neurotoxic effects observed in other experiments are due to neurotoxins produced by HIV-1 infecting PBMC, astrocytes or microglia.

Figure 9:
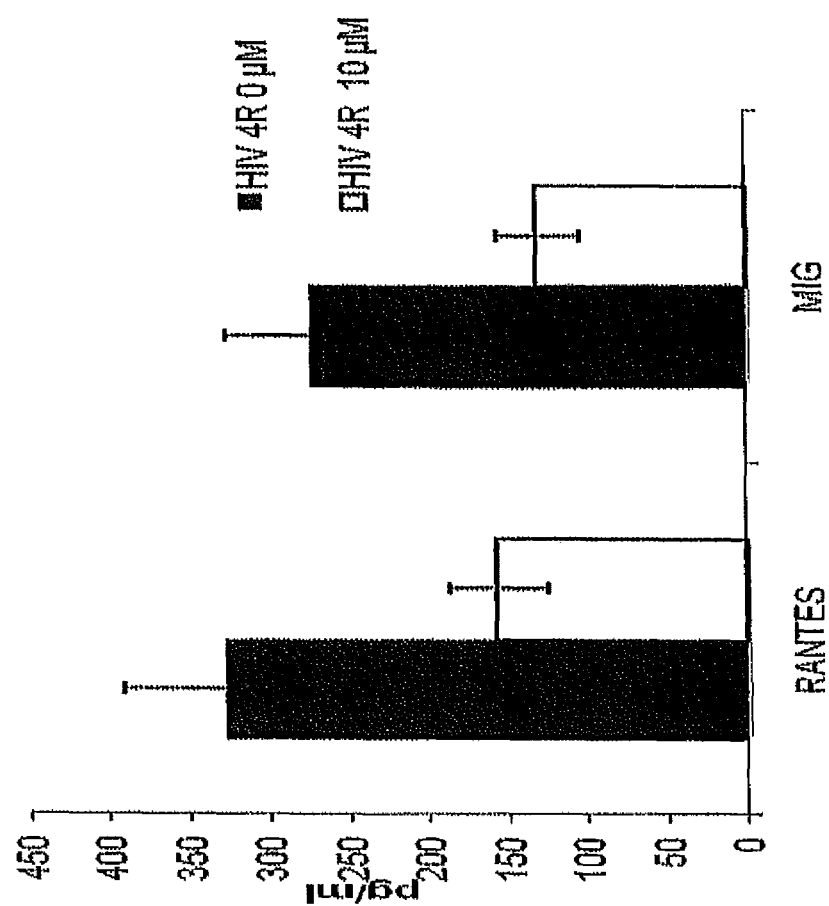
FIG. 9 shows graphical results of 4R decreasing the liberation of pro-inflammatory chemokines RANTES and MIG from PBMCs infected with HIV-1 virus.

FIG. 9 is directed to the effect of 4R on RANTES and MIG chemokines production in acutely HIV-1 infected PBMC. The PBMC were infected with HIV-1 SF2 for 6 days. Before infection cells were pre-treated with 4R (10 µM) for 24 hours; 4R (10 µM) was also added 24 hours after infection and at day 3. Control cultures received 4R vehicle (DMSO) at the same times. Cytokine release was measured by cytometric bead array (CBA).

The results show that with human PBMC acutely infected with HIV-1 virus, an amount of at least 10 µM 4R decreased the liberation of pro-inflammatory chemokines RANTES and MIG to approximately 50% of the control value obtained in the absence of 4R.

Figure 10:
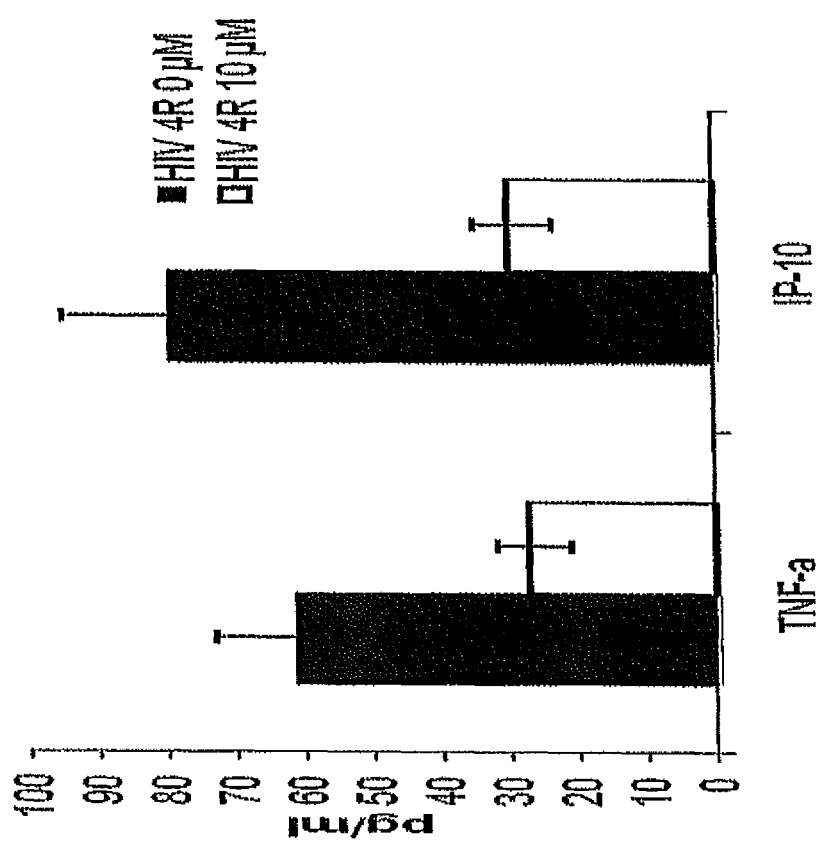
FIG. 10 shows graphical results of 4R decreasing the liberation of pro-inflammatory cytokines TNF-α and IP10 from PBMC infected with HIV-1 virus.

FIG. 10 is directed to the effect of 4R on TNF-α and IP-10 cytokines production in acutely HIV-1 infected PBMC.

PBMC were infected with HIV-1 SF2 for 6 days. Before infection cells were pre-treated with 4R (10 µM) for 24 hours; 4R (10 µM) was also added 24 hours after infection and at day 3. Control cultures received 4R vehicle (DMSO) at the same times. Cytokine release was measured by cytometric bead array (CBA).

The results show that with human PBMC acutely infected with HIV-1 virus, an amount of at least 10 µM 4R decreased the liberation of pro-inflammatory cytokines TNF-α and IP-10 to less than 50% of the control value obtained in the absence of 4R. This finding is very important since these two cytokines are closely associated with up-regulation of HIV-1 replication. Therefore, one mechanism by which 4R suppresses viral replication is by down-regulating the production of these pro-inflammatory cytokines.

Figure 11:
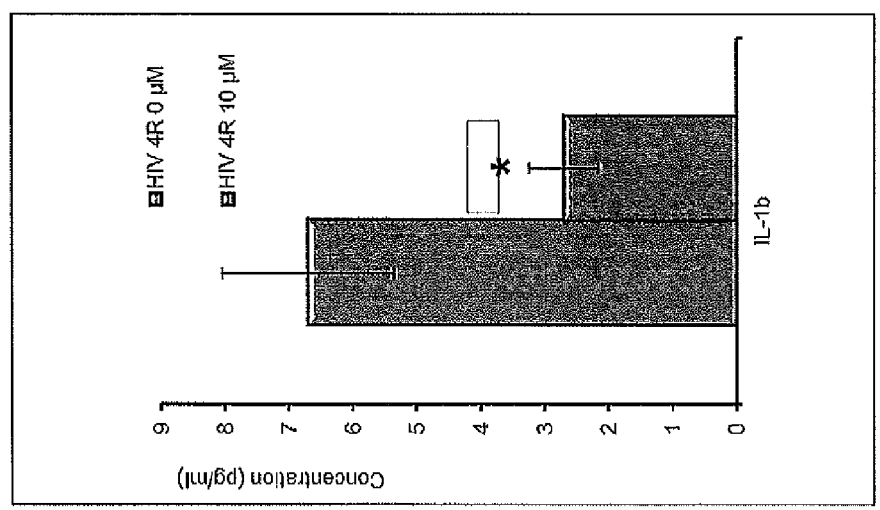
FIG. 11 shows graphical results of 4R decreasing the liberation of pro-inflammatory cytokines IL-1b from PBMC infected with HIV-1 virus.

FIG. 11 is directed to the effect of 4R on cytokine IL-1b production in acutely HIV-1 infected PBMC. Approximately $2.0 \times 10^6$ PBMC were infected with HIVSF2 strain for 24 hours. After washing with medium, the cells were treated with 10 µM 4R. At 6 days post-infection, supernatants were collected and subjected to inflammatory cytokine measurement using cytometric bead array (CBA).

The results showed that 4R inhibited the inflammatory cytokines IL-1b by 60%. This is important because the production of inflammatory cytokines is closely associated to HIV-1 replication and brain damage.

Figure 12:
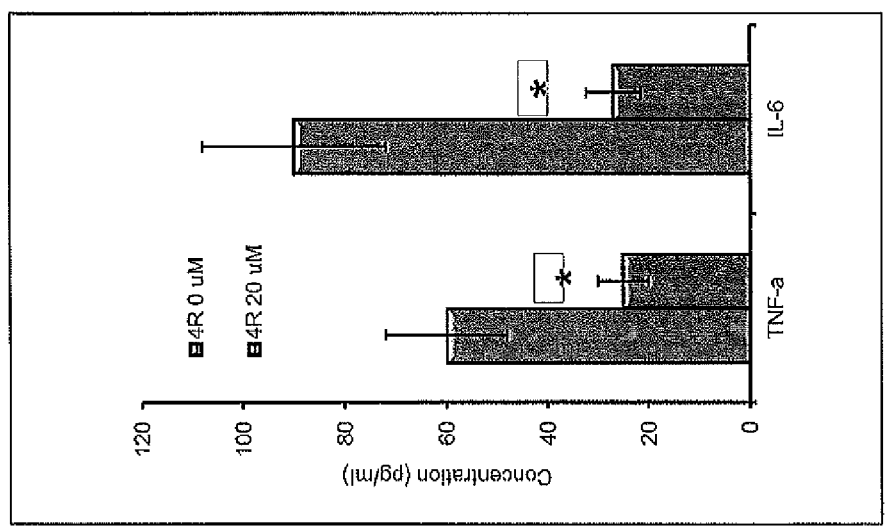
FIG. 12 shows graphical results of 4R decreasing the liberation of pro-inflammatory cytokines IL-6 and TNF-α from PBMC infected with HIV-1 virus.

FIG. 12 is directed to the effect of 4R on cytokines IL-6, and TNF-α production in acutely HIV-1 infected PBMC. Approximately $2.0 \times 10^6$ PBMC were infected with HIVSF2 strain for 24 hours. After washing with medium, the cells were treated with 20 µM 4R. At 6 days post-infection, supernatants were collected and subjected to inflammatory cytokine measurement using cytometric bead array (CBA).

The results showed that 4R inhibited the inflammatory cytokines IL-6 and TNF-α to 40% and 30% of control, respectively. This is important because the production of inflammatory cytokines is closely associated to HIV-1 replication and brain damage.

Figure 13:
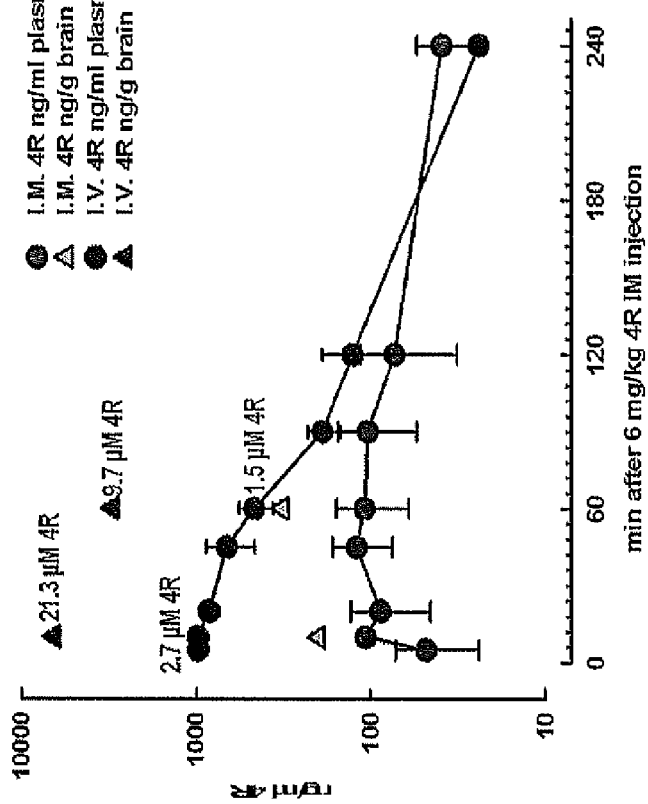
FIG. 13 shows graphical results of 4R penetrating and accumulating in the brain, where it will exert its neuroprotective activity.

FIG. 13 is directed to plasma and brain 4R levels in male Sprague-Dawley rats. Rats were administered 6 mg/kg 4R by either intravenous (iv) or intramuscular (im) routes. Blood was collected at several time points through 8 hr after administration and brains were collected at 2 time points. 4R levels were determined using an LC-MS/MS method. Values represent the mean±SD of 3 rats.

The results show that just 10 min after injection, 4R was found in brain at higher concentration than those seen in blood. Therefore, 4R penetrates into and accumulates in the brain where it can fulfill its neuroprotective activity.

Other methods to administrate 4R cembranoid to the subject are by intranasal route and by oral route. For intranasal route 4R cembranoid is administered to the subject in a dose range of 1 mg/kg to 90 mg/kg body weight. On the other hand for oral route 4R cembranoid is administered to the subject b in a dose range of 1 mg/kg to 120 mg/kg body weight.

Our results demonstrate that 4R was not toxic to glial cells at a concentration of 1-100 µM and to neurons at a concentration of 10 µM. Furthermore, 4R suppressed HIV-1 replication in T-lymphocytes and downregulated the inflammatory chemokines RANTES and MIG, and the inflammatory cytokines TNF-α and IP-10. In accordance with the principles of the present invention it is disclosed a method for using the compound 4R to prevent or alleviate the damaging effects following HIV-1 infection in the brain, more particularly the mechanisms involved in the pathogenesis of HAND by which this compound may elicits its properties. Further it is disclosed the mechanism by which 4R exerts its effect on lymphocytes and brain cells which leads to the development of therapy for treating HIV-1-induced encephalopathy.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentably distinguish any amended claims from any applied prior art.

The invention claimed is:

1. A method for treatment of an HIV-infected subject, comprising:
   administering to a subject an effective amount of a 4R cembranoid.

2. The method of claim 1 wherein the treatment of an HIV-infected subject is inhibiting replication of the HIV-1 virus strains, treating HIV virus-induced inflammation or treating HIV virus-induced neurocognitive disorders.

3. The method of claim 1, wherein the 4R cembranoid is administered to the subject in a dose range of 1 mg/kg to 120 mg/kg body weight.

4. The method of claim 3, wherein the 4R cembranoid is administered to the subject by an oral route.

5. The method of claim 1, wherein the 4R cembranoid is administered to the subject in a dose range of 3 mg/kg to 60 mg/kg body weight.

6. The method of claim 5, wherein the 4R cembranoid is administered to the subject intravenously.

7. The method of claim 1, wherein the 4R cembranoid is administered to the subject in a dose range of 6 mg/kg to 90 mg/kg body weight.

8. The method of claim 7, wherein the 4R cembranoid is administered to the subject by an intramuscular route.

9. The method of claim 1, wherein the 4R cembranoid is administered to the subject in a dose range of 1 mg/kg to 90 mg/kg body weight.

10. The method of claim 9, wherein the 4R cembranoid is administered to the subject by an intranasal route.

* * * * *